United States Patent [19]

Wurster

[11] Patent Number: 5,058,590

[45] Date of Patent: Oct. 22, 1991

[54] APPARATUS FOR DISPERSING FLUIDS FOR DISSOLUTION OR CONCRETIONS IN A BODILY CAVITY

[75] Inventor: Helmut Wurster, Oberderdingen, Fed. Rep. of Germany

[73] Assignee: Richard Wolf GmbH, Knittlingen, Fed. Rep. of Germany

[21] Appl. No.: 345,439

[22] Filed: May 1, 1989

[30] Foreign Application Priority Data

Apr. 30, 1988 [DE] Fed. Rep. of Germany ....... 3814743

[51] Int. Cl.$^5$ ............................................ A61B 17/22
[52] U.S. Cl. .......................... 128/660.03; 128/24 EL; 604/22; 310/335
[58] Field of Search ...................... 128/660.03, 663.01, 128/24 AA, 24 EL; 310/334–336; 606/128; 604/22

[56] References Cited

U.S. PATENT DOCUMENTS

| | | |
|---|---|---|
| 3,526,219 | 9/1970 | Balamuth . |
| 3,589,363 | 6/1971 | Banko et al. . |
| 4,183,249 | 1/1980 | Anderson . |
| 4,216,766 | 8/1980 | Duykers et al. . |
| 4,474,180 | 10/1984 | Angulo . |
| 4,587,958 | 5/1986 | Noguchi et al. . |
| 4,651,716 | 3/1987 | Forester et al. ................... 128/24 A |
| 4,721,106 | 1/1988 | Kurtze et al. . |
| 4,763,652 | 8/1988 | Brisson et al. . |
| 4,771,787 | 9/1988 | Wurster et al. ................ 128/660.03 |
| 4,869,278 | 9/1989 | Bran .................................... 310/335 |
| 4,942,868 | 7/1990 | Vago .................................. 128/24 A |

FOREIGN PATENT DOCUMENTS

| | | |
|---|---|---|
| 2913251 | 8/1985 | Fed. Rep. of Germany . |
| 1268161 | 11/1986 | U.S.S.R. ............................ 128/24 A |
| 2140693 | 12/1984 | United Kingdom . |
| 2176110 | 12/1986 | United Kingdom . |

OTHER PUBLICATIONS

Wurster, Ziegler and Marberger, "Chapter VI, Piezolith 2200 (Richard Wolf GmbH)," *Lithotripsy II*, Coptcoat, Miller and Wickham, eds., pp. 91–107 (Sep. 1987).

P. P. Lele, "Cavitation and its Effects on Organized Mammalian Tissues, A Summary," *Methods and Phenomena 3—Ultrasound; Its Application in Medicine and Biology, Part II*, F. J. Fry, ed., Elsevier Scientific Pub. Co., 1978, pp. 737–741.

*Primary Examiner*—Ruth S. Smith
*Attorney, Agent, or Firm*—Panitch Schwarze Jacobs & Nadel

[57] ABSTRACT

Apparatus for dissolving concretions within a bodily cavity, for example in the gall bladder, under the action of a solvent fluid applied within the bodily cavity, comprises an ultrasonic transducer arranged to be coupled to the exterior of the patient's body and to be focussed on selected parts of the bodily cavity. The transducer emits ultrasonic waves within a frequency range of between 20 and 40 kHz and with just enough power to generate cavitations in bodily cavity fluid within the body cavity, or in the solvent fluid, or in both of these fluids to cause dispersion therebetween.

6 Claims, 2 Drawing Sheets

APPARATUS FOR DISPERSING FLUIDS FOR DISSOLUTION OR CONCRETIONS IN A BODILY CAVITY

FIELD OF THE INVENTION

This invention relates to apparatus for, and a method of, dissolving concretions within a bodily cavity of a patient to be treated.

BACKGROUND OF THE INVENTION

It is customary in clinical treatment for eliminating concretions within a bodily cavity, for example of stones within a kidney, to destroy them by means of ultrasonic shock waves, particles of concretion remaining in the bodily cavity being flushed out by way of natural outlets or drawn off by means of a suction and flushing pump.

Long experience in the clinical use of so-called "ultrasonic lithotriptors", has taught that treatment therewith does not succeed in all applications on account of anatomical conditions, amongst other factors. The destruction of stones within the gall bladder is an example of a clinical field in which ultrasonic lithotriptors can only conditionally be used, such limited usability being attributable to the fact that particles produced by the disintegration of a gall stone cannot pass through the ductus cysticus, or cannot pass therethrough completely.

Another method of removing concretions from bodily cavities, the application of which depends upon the nature of the concretions, is by use of a solvent. In this method, the solvent is commonly infed by puncturing the skin of the patient. A disadvantage of this method is, however, that the dissolution of a concretion by the solvent is comparatively protracted. Also, the infeed of the solvent through the patient's skin and the required draining of bile through the skin are distressing to the patient. Such protracted dissolution is, amongst other things caused by the fact that the solvents usually selected are lighter than the bile so that the solvents increasingly accumulate on the bile secreted during treatment whereby their effectiveness is reduced.

SUMMARY OF THE INVENTION

In the light of the foregoing it is an object of the present invention to provide for the treatment of concretions within bodily cavities whereby the bile and the solvent are mixed so that the solvent can better act upon the concretions to be dissolved and the time taken for their dissolution is substantially reduced.

According to one aspect of the invention, therefore, apparatus for the dissolution of concretions within a bodily cavity, for example within the gall bladder, with the use of a solvent applied within said cavity, comprises an ultrasonic transducer arranged to be coupled extracorporeally to the patient and to be focussed on the interior of said bodily cavity and which emits ultrasonic waves within a frequency range of 20 to 40 kHz with sufficient power to produce cavitations within the fluid of the bodily cavity and/or in the solvent thereby to cause dispersion between the solvent and said fluid.

Said dispersion between the bodily fluid and the solvent, produced by said cavitations, allows the surface of the concretion to be dissolved to be constantly laved by the solvent, thereby substantially increasing the dissolving action of the solvent on the concretion. The disadvantage mentioned above, arising from the difference in density between the bodily cavity fluid and the solvent, is accordingly avoided.

Briefly stated, the apparatus may be said to comprise an ultrasonic transducer, which can be coupled to the patient extracorporeally and focussed and which transmits ultrasonic waves within a frequency range of between 20 and 40 kHz with sufficient energy to generate said cavitations. Said energy should, however, be insufficient to cause disintegration of the concretion to be dissolved, in the manner of the energy applied by an ultrasonic lithotriptor.

According to the embodiment of the invention, the ultrasonic transducer is in the form of a sandwich structure having a concave end for coupling to the surface of the body, for example by way of a water filled flexible bag and is advantageously shaped for focussing the ultrasonic waves on selected treatment areas of the bodily cavity, to produce said dispersion.

According to another embodiment of the invention, the ultrasonic transducer is a spherical ultrasonic resonator.

A locating system may be associated with the transducer to allow of verifying the extent of dissolution of the concretion to be dissolved, during treatment. The locating system may, for example, comprise a B scanner or such verification may be effected by an X-ray system technique.

According to another aspect of the invention a method of dissolving a concretion within a bodily cavity, whereby the action of the solvent on the concretion to be dissolved is substantially intensified, comprises the steps of:

introducing a fluid solvent for dissolving the concretion into said bodily cavity; and applying to the fluid of the bodily cavity and/or to the solvent, ultrasonic waves having a frequency range of 20 to 40 kHz and just sufficient power to produce dispersion between said fluid and said solvent by generating cavitations in said fluid and/or in said solvent.

The solvent may be ducted into the bodily cavity by way of natural bodily passages, by means of an endoscope or a catheter inserted thereinto. The solvent may, however, be fed into the bodily cavity by a puncturing method.

The extent of the dissolution of the concretion to be dissolved may be checked during treatment, by means of a locating system.

By means of the apparatus and method described herein, there is achieved rapid dissolution of the concretions to be removed, or of stone particles in the bodily cavity produced by disintegration of the concretions and which cannot be completely removed or indeed cannot be removed at all, by natural methods. Apart from being used to remove bodily concretions by the use of ultrasonic shock waves, the method may alternatively be used, for example, as a complementary expedient for the elimination of concretion particles. The use of such a method is in any event preferable to a surgical operation.

DETAILED DESCRIPTION OF THE INVENTION

Figure 1:
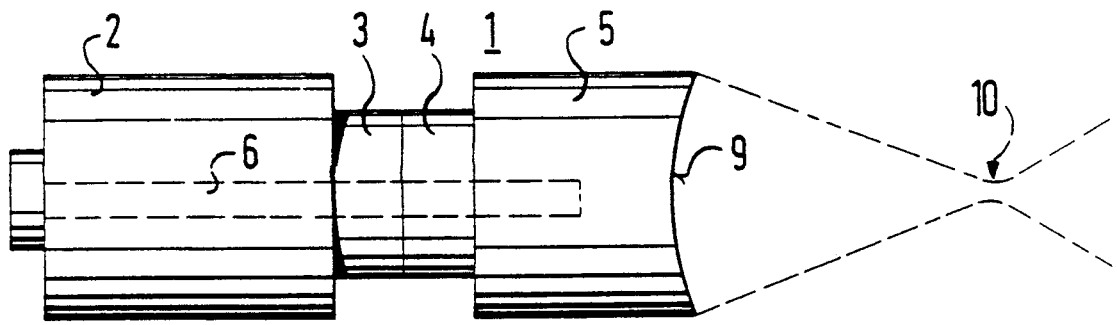
FIG. 1 is a diagramatic elevational view of an ultrasonic transducer having a sandwich structure, according to one embodiment of the invention.

As shown in FIG. 1 an ultrasonic transducer 1 of sandwich construction comprises a steel member 2, piezo-electric ceramics plates 3 and 4 and an aluminum member 5, all firmly joined together by means of a bolt 6 in juxtaposed relationship with the plates 3 and 4 between the members 2 and 5. The plates 3 and 4 are electrically connected to a generator 35 (FIG. 3) by means of a lead, and electrical terminals (not shown). The generator 35 emits electrical oscillations which are converted into mechanical ultrasonic oscillations of the piezoelectric plates 3 and 4.

The aluminum member 5 of the transducer 1 has a concave end surface 9 at that end of the transducer 1 which is to be coupled to the surface of a body to be treated.

The concave surface 9 causes ultrasonic waves generated by the transducer 1 to be focussed at a focal point 10.

Figure 2:
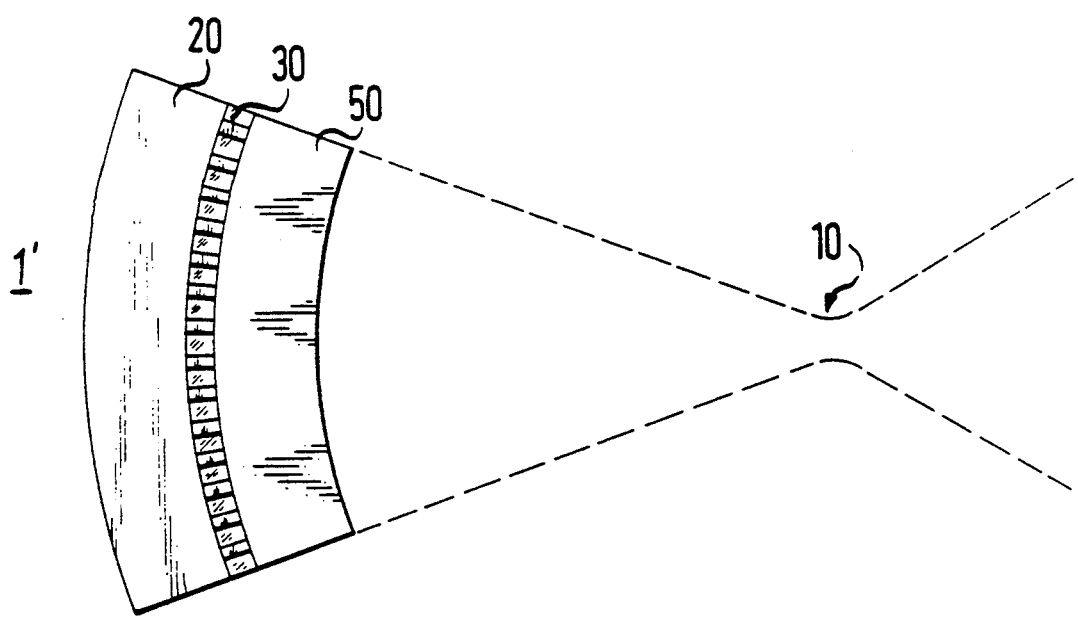
FIG. 2 is a diagramatic elevational view of an ultrasonic transducer in the form of a spherical resonator according to another embodiment of the invention.

As shown in FIG. 2 an ultrasonic transducer 1' is constructed as a spherical resonator comprising a spherical steel member 20, a spherical ceramics layer 30 of piezo-electric ceramics elements, and spherical aluminum member 50, secured together in juxtaposed relationship with the layer 30 between the members 20 and 50. When connected electrically to a generator 35 the transducer 1' transmits ultrasonic waves produced by the layer 30, which are focussed at a focal point 10.

The transducer shown in FIG. 1, or FIG. 2, is energized by its generator 35 to emit ultrasonic waves within a frequency range of from 20 to 40 kHz and with such power as to suffice to generate cavitations in the fluid of a bodily cavity containing a concretion to be dissolved and/or in a fluid solvent that has been applied in said cavity. To this end, the focus of the transducer coincides with the internal volume of said bodily cavity.

Within the specified frequency range, a power of 5 watts/sq. cm will be sufficient to produce the desired cavitation.

After the solvent for the concretion has been fed into the bodily cavity, the transducer is energized as described above so that the solvent forms a dispersion with the bodily cavity fluid within the bodily cavity. The action of the solvent on the concretion which is to be dissolved is thereby intensified considerably.

Figure 3:
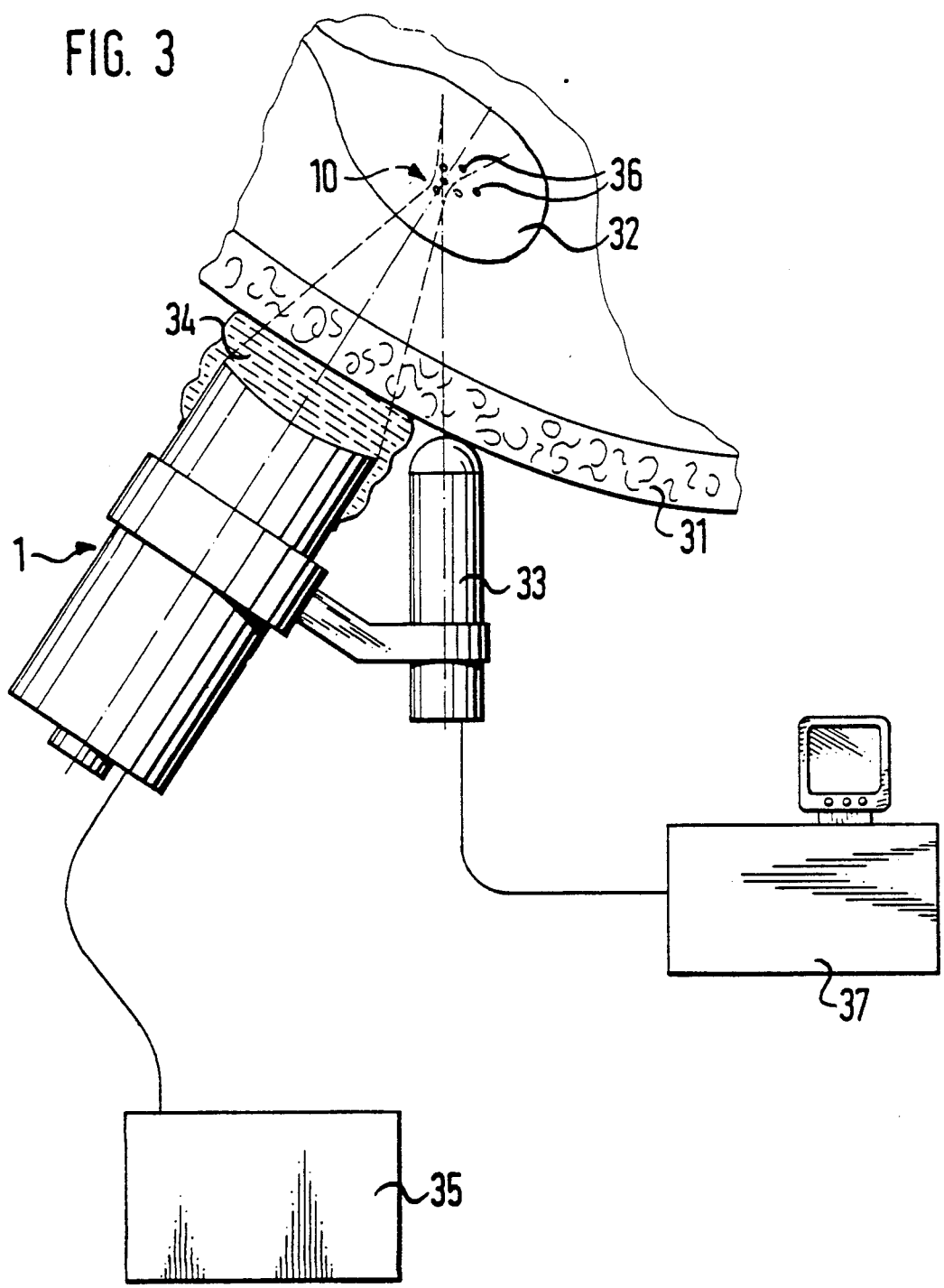
FIG. 3 is a diagram illustrating the use of apparatus for the dissolution of concretions in the gall bladder by means of a transducer according to FIG. 1.

FIG. 3 illustrates the use of apparatus comprising the transducer 1 in treatment for the dissolution of a concretion 36, in the form of a gall stone or gall stones, within a gall bladder 32. The ultrasonic waves emitted by the transducer 1 are focussed on the focal point 10 which coincides with the interior of the gall bladder 32. The coupling of the transducer 1 to the surface 31 of the body to be treated is effected in a known manner, for example by way of water filled flexible bag 34. The transducer 1 is energized by means of the generator 35 in this example.

The transducer 1 shown in FIG. 3 has a locating system 33 constructed as a B scanner in the example illustrated, the output signals of which are depicted on a monitor 37 in known manner. Several locating systems may also be used for displaying said gall stone or gall stones.

Apart from locating the concretion 36 and positioning the concretion 36 at the focus of the transducer 1, the degree of dissolution of the concretion 36 can be checked during the treatment, so that the solvent can be cyclically or continuously replaced if this is required to maintain the action of the solvent.

Such observation could otherwise be carried out by X-ray technique, by means of an X-ray system (not shown).

A method according to the invention for the dissolution of said concretion (or calculus) 36 within a bodily cavity, for example within a gall bladder 32, includes the following two steps:

1. A solvent fluid for dissolving the concretion 36 is introduced into the bodily cavity containing the concretion. This may be performed by penetration or by way of natural bodily passages by means of an endoscope and/or a catheter inserted therein.

2. The bodily cavity fluid and the solvent fluid are acted upon by ultrasonic waves. To this end, the ultrasonic waves have a frequency of between 20 and 40 kHz and such power as to suffice barely to generate cavitations to produce dispersion between the bodily cavity fluid and the solvent fluid.

The degree of dissolution of the concretions in the bodily cavity fluid is preferably checked throughout the treatment by means of a locating system. This enables the physician continuously to observe the action of the solvent, so that the same can be supplemented used or replaced entirely upon the basis of such observation. Different kinds of locating system may be used for observation purposes depending on the degree of resolution that is needed, for example a B scanner is used to provide coarser resolution and an X-ray system to provide more precise resolution. In other respects the choice of locating system depends upon the position of the bodily cavity in which the concretion to be dissolved is situated within the body. An ultrasound locating system (for example a B scanner) is to be preferred, however, in the light of all the prevailing factors, in the interest of subjecting the patient to a minimum incidence of radiation.

I claim:

1. Apparatus for dissolving concretions within a bodily cavity of a patient to be treated, under the action of a solvent fluid in contact with bodily cavity fluid within said cavity, the apparatus comprising means for introducing a solvent fluid into said bodily cavity for mixture with said bodily cavity fluid, an ultrasonic transducer adapted for coupling to the exterior of the patient's body, and being provided with means for emitting ultrasonic waves focussed on at least one of said fluids in said cavity, within a frequency range of from 20 to 40 kHz and having sufficient power to produce cavitation in at least one of said fluids to cause dispersion therebetween.

2. Apparatus as claimed in claim 1, wherein said transducer is of sandwich construction and has a concave end surface for coupling to said exterior of the patient's body.

3. Apparatus as claimed in claim 2, wherein said transducer comprises a steel member, a pair of juxtaposed piezo-electric ceramic plates and an aluminum member in which said concave end surface is formed, said steel and aluminum members being secured together with said ceramic plates therebetween, and said apparatus further comprises a generator for producing electrical oscillations, and means connecting said ceramic plates to said generator.

4. Apparatus as claimed in claim 1, wherein said ultrasonic transducer is a spherical ultrasonic resonator.

5. Apparatus as claimed in claim 4, wherein said transducer comprises a steel member, a layer of piezoelectric ceramic elements, and an aluminum member secured together in juxtaposed relationship with said layer of ceramic elements between said steel member and said aluminum member, and said apparatus further comprises a generator for producing electrical oscillations, and means for connecting said ceramic elements to said generator.

6. Apparatus as claimed in claim 1, wherein said transducer is provided with locating means for establishing the position of said concretions in said bodily cavity, for aligning the focus of said transducer with said concretions, and for establishing the extent of dissolution of said concretions.

* * * * *